(12) United States Patent
Bouhelier et al.

(10) Patent No.: US 7,333,205 B2
(45) Date of Patent: Feb. 19, 2008

(54) BROADBAND SURFACE PLASMON JETS: DIRECT OBSERVATION OF PLASMON PROPAGATION FOR APPLICATION TO SENSORS AND OPTICAL COMMUNICATIONS IN MICROSCALE AND NANOSCALE CIRCUITRY

(75) Inventors: Alexandre Bouhelier, Westmont, IL (US); Gary P. Wiederrecht, Elmhurst, IL (US)

(73) Assignee: U Chicago Argonne LLC, Chicago, IL (US)

( * ) Notice: Subject to any disclaimer, the term of this patent is extended or adjusted under 35 U.S.C. 154(b) by 162 days.

(21) Appl. No.: 11/230,281

(22) Filed: Sep. 19, 2005

(65) Prior Publication Data
US 2006/0221343 A1 Oct. 5, 2006

Related U.S. Application Data

(60) Provisional application No. 60/666,901, filed on Mar. 31, 2005.

(51) Int. Cl.
*G01N 21/55* (2006.01)

(52) U.S. Cl. .................................................. 356/445
(58) Field of Classification Search ............... 356/445, 356/128, 134–136
See application file for complete search history.

(56) References Cited

U.S. PATENT DOCUMENTS

2004/0100636 A1* 5/2004 Somekh et al. ............. 356/497
2005/0185186 A1* 8/2005 Smolyaninov et al. ...... 356/445

FOREIGN PATENT DOCUMENTS

WO    WO 0120295 A2 *   3/2001

\* cited by examiner

*Primary Examiner*—Tarifur Chowdhury
*Assistant Examiner*—Jonathan M Hansen
(74) *Attorney, Agent, or Firm*—Foley & Lardner LLP

(57) ABSTRACT

A system and method for generating and using broadband surface plasmons in a metal film for characterization of analyte on or near the metal film. The surface plasmons interact with the analyte and generate leakage radiation which has spectral features which can be used to inspect, identify and characterize the analyte. The broadband plasmon excitation enables high-bandwidth photonic applications.

18 Claims, 16 Drawing Sheets

SE 05-Nov-03 LNIO WD7.7mm 3.00kV x12k 2.5μm

BSE1 05-Nov-03 LNIO WD10.0mm 25.0kV x50k 1μm

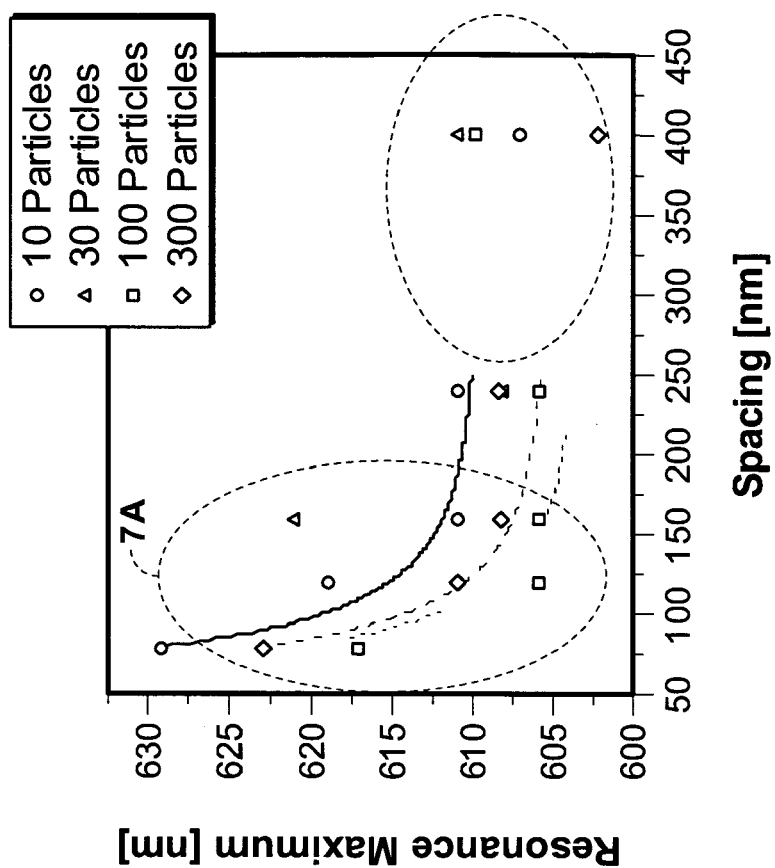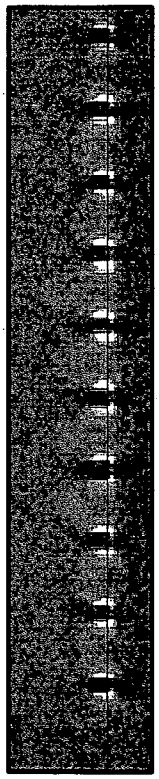
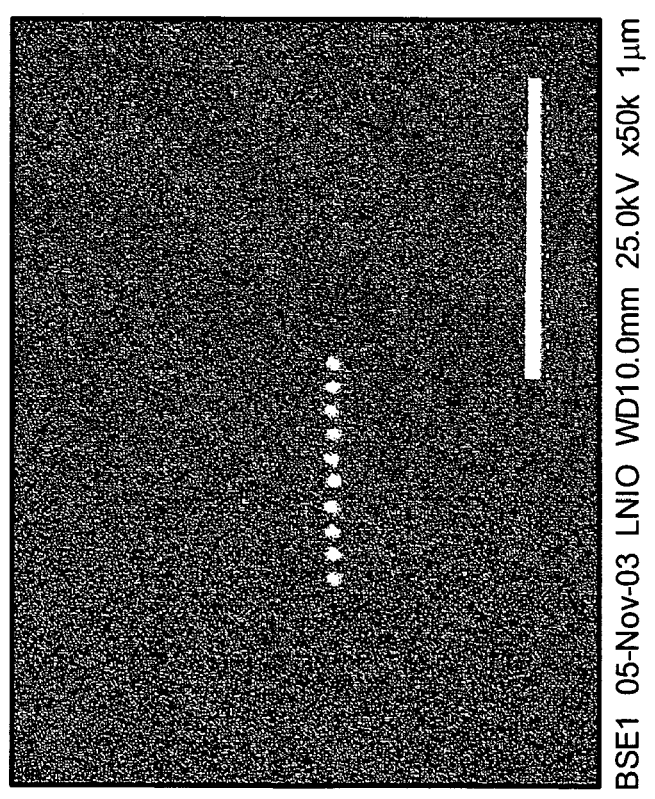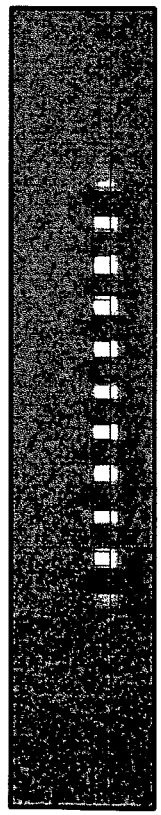
FIG. 7A
FIG. 7B

S-4700 1.0kV 12.3mmx4.00k SE(L) 3/17/04 09.56 10.0μm

BROADBAND SURFACE PLASMON JETS: DIRECT OBSERVATION OF PLASMON PROPAGATION FOR APPLICATION TO SENSORS AND OPTICAL COMMUNICATIONS IN MICROSCALE AND NANOSCALE CIRCUITRY

CROSS-REFERENCE TO RELATED PATENT APPLICATIONS

This application claims priority to U.S. Provisional Patent Application No. 60/666,901 filed on Mar. 31, 2005, and is incorporated herein by reference.

The United States Government has certain rights in this invention pursuant to Contract No. W-31-109-ENG-38 between the U.S. Department of Energy and The University of Chicago operating Argonne National Laboratories.

FIELD OF THE INVENTION

This invention relates to a method for optically exciting and detecting surface plasmons in thin metal films, schematically illustrated in FIG. 1. More specifically this invention relates to a method for the excitation and detection of surface plasmons having a broad wavelength spectrum. Still more specifically this invention relates to a method for the excitation of surface plasmons which have utility for propagating plasmons in metal films, with applications in photonics. This invention also relates to the spectroscopy and sensing of adsorbates on metal films using the broadband plasmon feature. In addition the invention relates to use of surface plasmons for optical communications in microscale and nanoscale circuitry.

BACKGROUND OF THE INVENTION

A plasmon is the quantization of plasma oscillations, which are density waves of the charge carriers in a conducting medium such as a metal, semiconductor, or plasma. Surface plasmons exist in various geometries, such as nanoparticles or two dimensional films. Thin film plasmons propagate in the micron range depending on the wavelength and type of material. Such plasmons are non-radiative in air and are sensitive to dielectric environment. Recent technological advances that allow metals to be structured and characterized on the nanometer scale triggered new interest in the application of surface plasmons (SPs). The control of SP properties is of interest to a wide spectrum of scientists, ranging from physicists, chemists and materials scientists to biologists. For instance, SPs are being explored for their potential in small-scale optical circuitry, high-resolution optical microscopy and bio-detection.

Surface plasmons are known solutions of Maxwell's equations applied along an interface between a medium with a negative permittivity, i.e. a metal, and a dielectric. These solutions are traveling waves that are generally bound to the interface and are exponentially decaying in both media. The optical excitation of surface plasmons on flat metal interfaces is challenged by the phase matching condition between the plasmons and the exciting radiation. The surface plasmon dispersion $\omega(k)$ is located outside the light cone $\omega=ck$ and hence no SPS can be excited with freely propagating radiation. The excitation of surface plasmons can only occur if the photon momentum—or the wave vector—can be artificially increased. Various experimental techniques have been developed to accomplish this task, such as (i) increasing the index of refraction of the incident medium (total internal reflection (TIR) conditions) or (ii) engineering the surface of the film (grating coupler). While these approaches provide very efficient coupling between the incident photons and the SP waves, the interaction area is usually comparable or greater than the SP propagation distances.

It was recognized very early that in an asymmetric structure, i.e. a thin metal film (permittivity $\epsilon_m$) surrounded by two dielectric media (permittivities $\epsilon_1$, and $\epsilon_2$, with $\epsilon_1 > \epsilon_2$), has four modes that are solutions of the dispersion relations. Two of these solutions exist at each of the interfaces $\epsilon_m/\epsilon_i$, i=1, 2) and are characterized by their fields decaying exponentially into the media. The two other modes are radiative leaky waves originating from the finite thickness of the film. As a non-radiative mode travels along an interface, the wave amplitude decays exponentially in the metal and is coupled into leakage radiation ("LR") by the opposite interface. The far-field observation of this leakage radiation (LR) gives a direct measurement of the non-radiative surface plasmon propagation at the opposite interface. The intensity of the radiation, at a given lateral position in the film, is proportional to that of the SP—at the same position.

Surface plasmons are thus well-known phenomena and commercial surface plasmon-based sensors are currently used in biological research and in industrial applications. Use of the surface plasmons allows manipulation of light in devices smaller than the wavelength and can be extremely localized. They also exhibit ultrafast dynamics for use in rapidly changing circumstances or for rapid data output. For example, the detection principle of a commercially available plasmon sensor relies on the surface plasmon resonance resulting from energy and momentum being transformed from incident photons into surface plasmons. This process is sensitive to the refractive index of the medium on the opposite side of the film from the reflected light. Heretofore, the light source used for optically exciting surface plasmons was a monochromatic laser directed at an angle through a prism to a metal (gold or silver) coated surface. The sensor operated by determining the variation in the angle of incidence for maximum plasmon absorption. The presence of an adsorbate material on the surface of the metal was detected by measuring the change in the angle of incidence of the monochromatic beam. Alternatively, the angle of incidence was fixed and the wavelength varied to extract the same information. These methods are, however, very time consuming and technically more difficult if one wishes to extract spectral information, e.g. multiple wavelengths, on the adsorbates material.

Further, in the vast majority of other surface plasmon studies, they are optically excited in the so-called Kretschmann attenuated total internal reflection ("ATR") configuration, where the momentum mismatch between free-propagating photons and SPs is taken from a material with a refractive index larger than air, e.g. a glass substrate. In the case of an ATR geometry and for smooth metal films, the leakage radiation ("LR") interferes destructively with the incoming excitation light at the reflection spot and cannot be detected if the excitation area is larger or comparable to the lateral decay length of the surface plasmon. However, if surface plasmons are locally excited by electrons or near-field techniques, LR can be observed. This is, however, technologically ambitious and difficult because near-field optics is based on scanning probe microscopy.

SUMMARY OF THE INVENTION

The invention is directed to a new system and method for the excitation and detection of a large spectrum of surface plasmons. With the increasing trend towards the miniaturization of photonic circuits, the confined nature of surface plasmons and their long propagation length make them suitable for integration in metallic planar circuitry designs. Rudimentary surface plasmon ("SP") optical manipulations in structured thin films include propagation, interference, scattering, waveguiding, splitting and mirror-like reflection. Due to the evanescent nature of the SP field traveling at the metal/air interface, near-field and fluorescence techniques were applied to image the surface plasmon intensity distributions and have been essential in the characterization of SP devices.

The preferred technique utilizes an incident white-light continuum beam as a excitation source and an index-matched immersion objective lens having a wide aperture in contact with the substrate being probed. The objective can be part of a conventional inverted optical microscope focused on the metal/glass interface. Importantly, the focusing of the white light continuum through the microscope objective produces a wide range of incident angles of excitation, so as to simultaneously launch a continuum of plasmons. This method and system enables an unusually large bandwidth or frequency of plasmons to be excited rather than the very narrow bandwidth of previous methods. Detection of the surface plasmon continuum is achieved by monitoring the leakage radiation including a continuum of wavelengths, including the visible and infra-red spectral region which has originated from the propagation of the surface plasmons. The radiation is recorded by a conventional CCD camera placed in an image plane. The instantaneous detection of the wide radiation bandwidth permits a new form of spectroscopy of adsorbates on the surface of the metal film.

BRIEF DESCRIPTION OF THE DRAWINGS

FIG. 7A illustrates red-shift of leakage radiation for smaller range particle spacing and FIG. 7B the effect for larger range particle separation;

DETAILED DESCRIPTION OF THE PREFERRED EMBODIMENTS

Figure 1A:
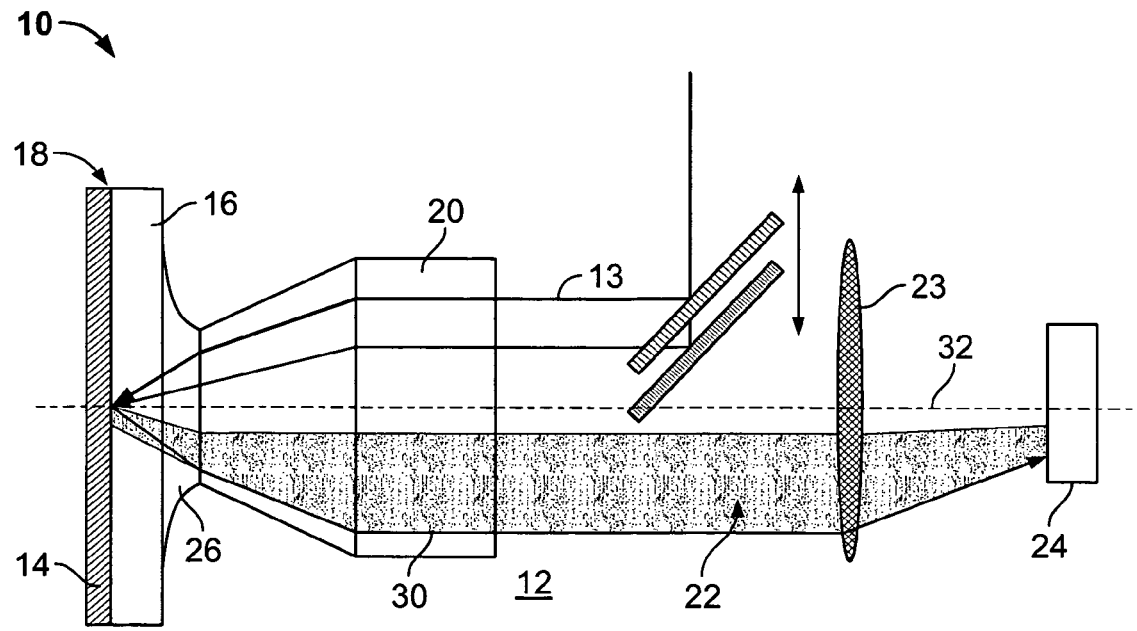
FIG. 1A illustrates a system for excitation and detection of surface plasmons.
Figure 1B:
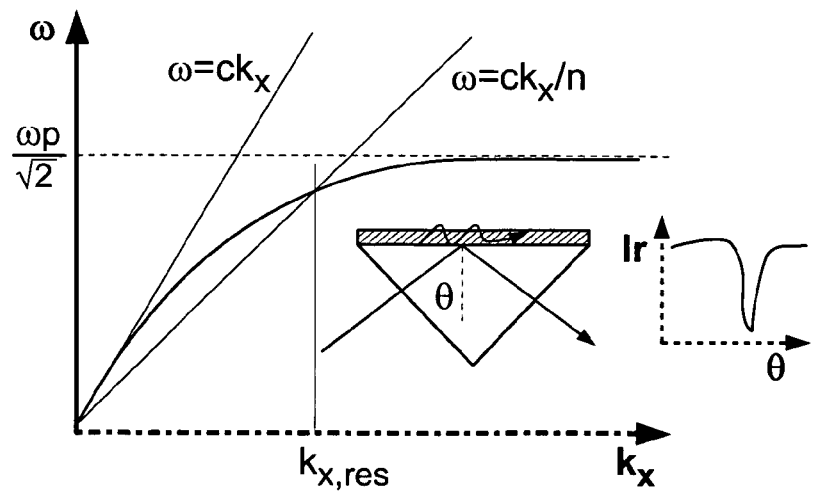
FIG. 1B illustrates plasmon frequency versus reciprocal space vector $k_x$.
Figure 1C:
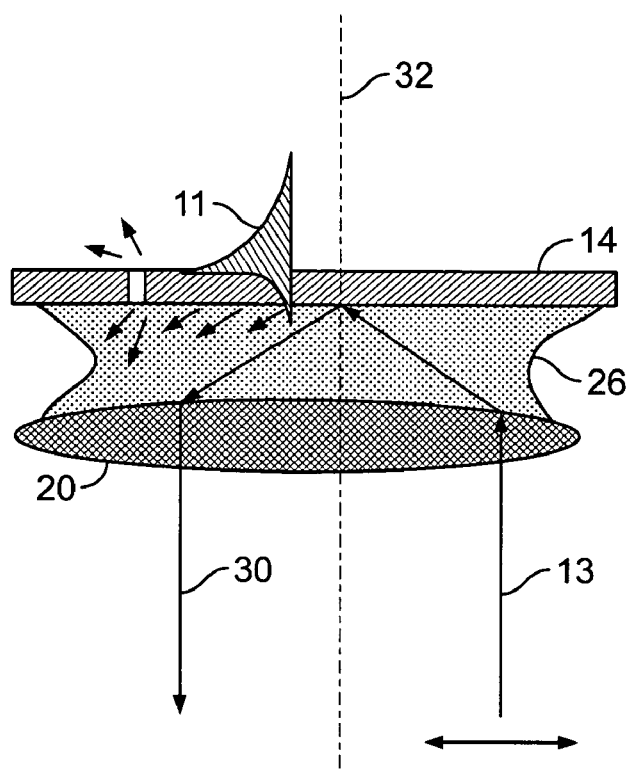
FIG. 1C illustrates a detail of surface plasmon creation from incident white light and coupling out of the material of leakage radiation.

A plasmon sensor system 10 constructed in accordance with a predefined form of the invention as illustrated in FIGS. 1A-1C. The plasmon sensor system 10 both creates surface plasmons 11 (see FIG. 1C) in a material and also detects those surface plasmons 11 in the form of an emitted continuum of photon wavelengths (leakage radiation) throughout the visible and infra-red region. Most preferably, the visible light spectrum is used to sense the surface plasmons 11 and their character which is representative of surface and near surface constituents 15 (see FIG. 11) of an underlying metal film or other metallic conductor. Heretofore, the dispersion relating the surface plasmon energy to the momentum has prevented the excitation of the surface plasmons 11 with a large spectral content due to the difficulty of attaining the necessary spread of momenta while keeping a low background signal for the attenuated total internal reflection ("ATR"). The broad-band surface plasmons 11 can be useful to investigate wavelength-sensitive planar photonic devices or to spectrally study adsorbates (or the constituents 15) on materials in which the surface plasmons 11 exist, such as, metal films (such as Ag or Au). This methodology has particular advantages for use in nanotechnology applications (See, for example, FIGS. 2A-2C, 3, 4, 5A, 5B, 6A, 6B, 7A and 7B).

As shown in FIGS. 1A-1C, an incident white-light beam 13 is applied to a material to generate the desired surface plasmons 11. The surface plasmon propagation is visualized by recording the real-space distribution of leakage radiation 22 emitted by the surface plasmon continuum as it travels along an asymmetric air 12/silver 14/glass structure 16. The surface plasmon 11 can be detected by scattering at defects and leakage radiation emitted back in the substrate (the silver 14).

Figure 10A:
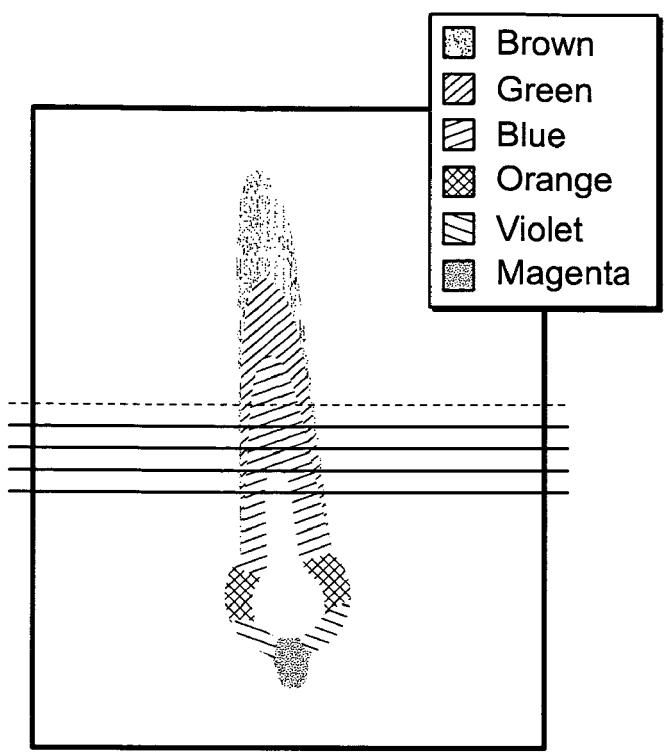
FIG. 10A illustrates the plasmon rainbow radiation with sections at different spacing from the origin with FIG. 10B showing intensity changes for a number of the spacing sections of FIG. 10A.
Figure 10B:
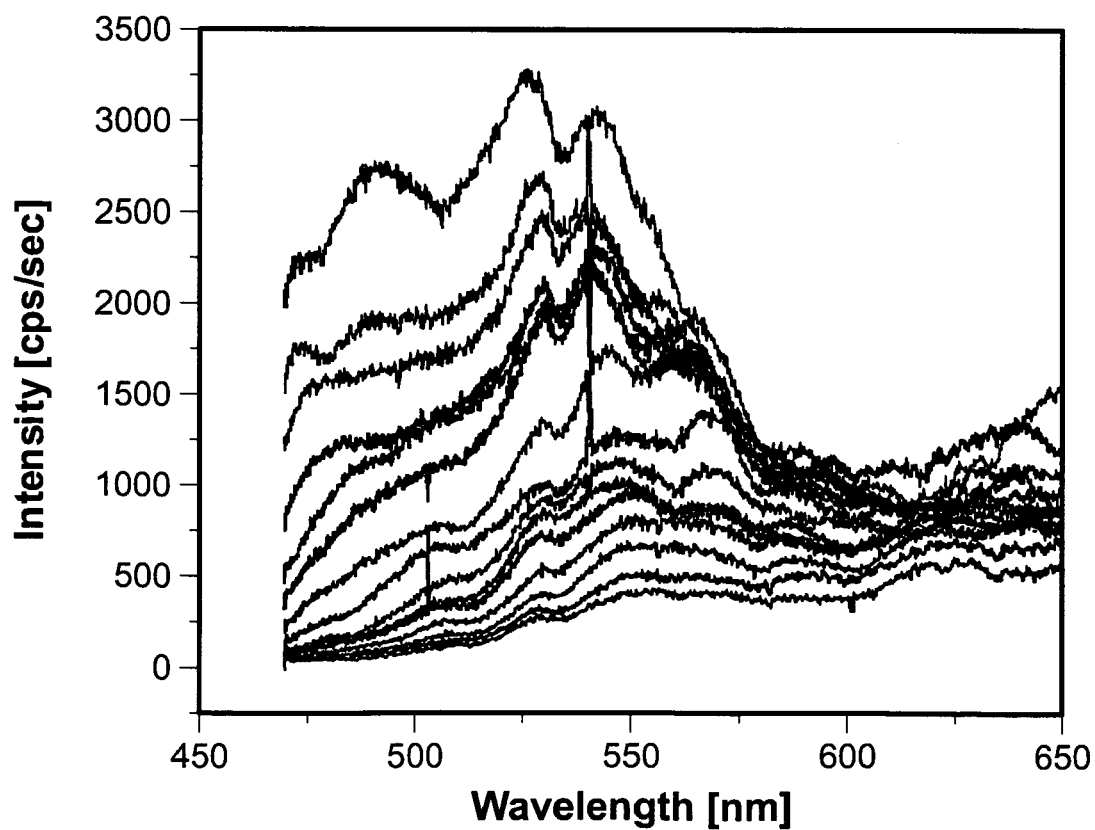
FIG. 10C illustrates exponential decay of leakage radiation intensity for different propagation distance and for different radiation wavelengths.
FIG. 10D illustrates plasmon decay length versus radiation wavelength.
Figure 10C:
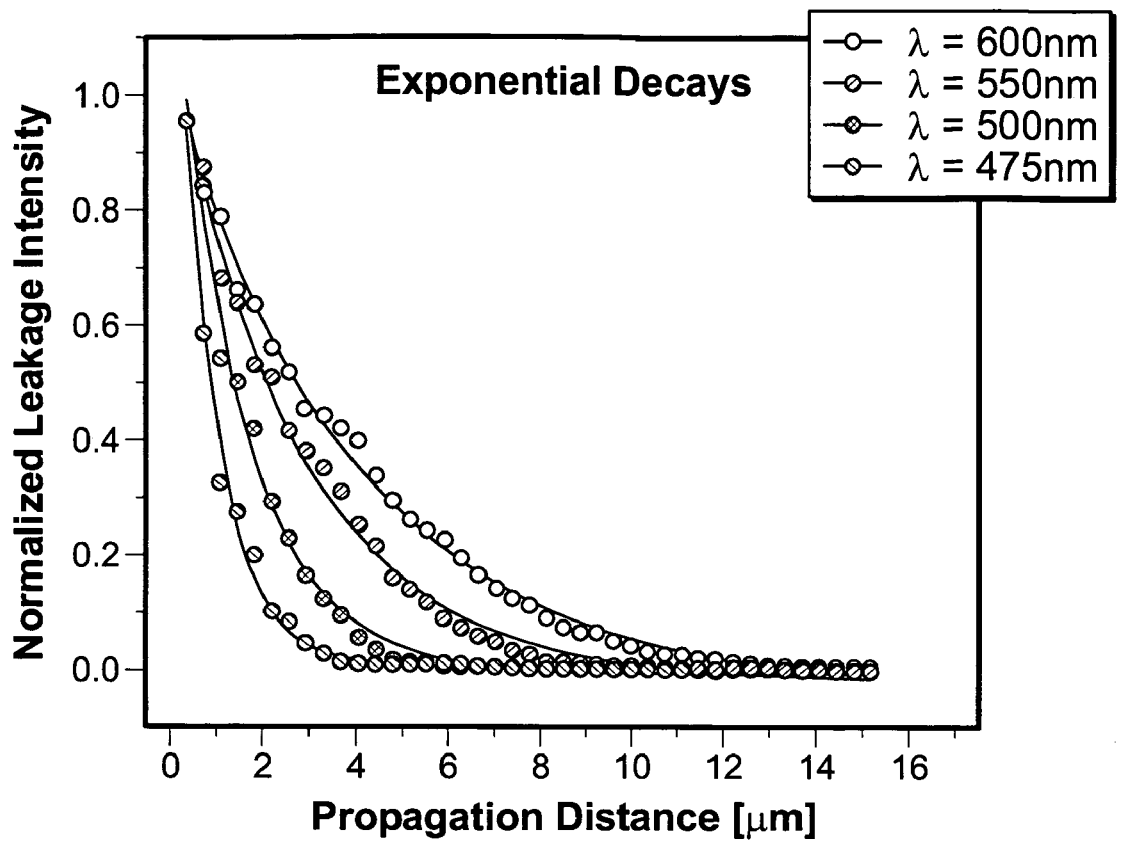
Figure 10D:
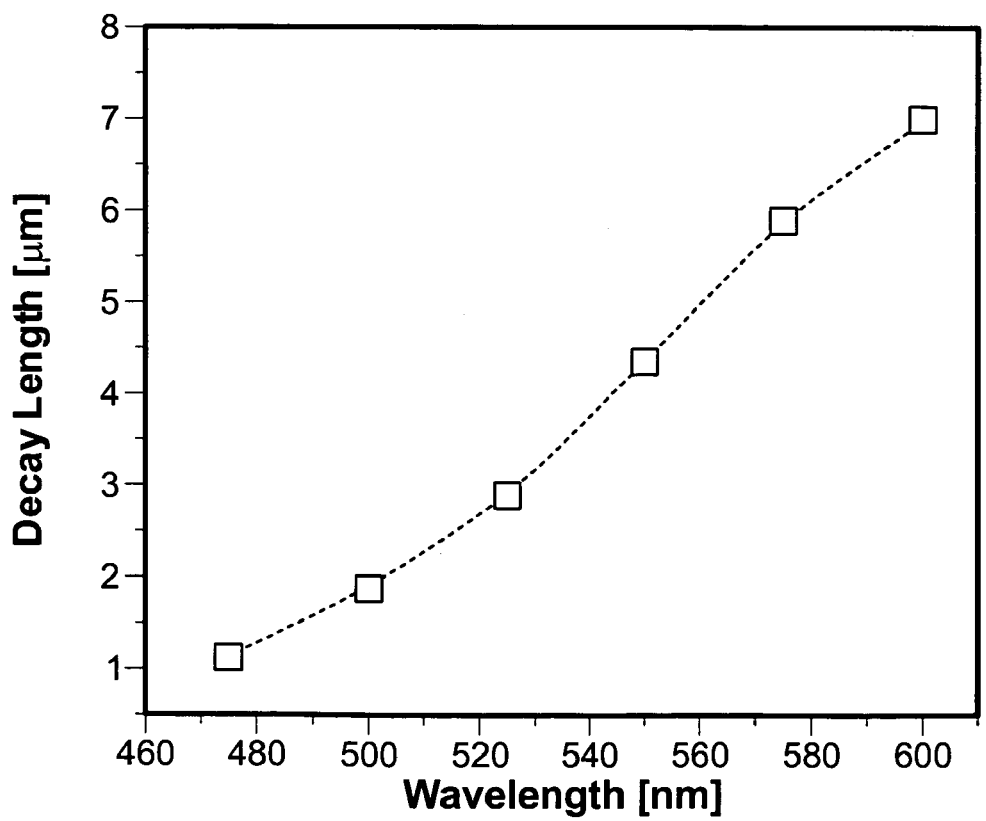

A spatial variation of the spectral components of the surface plasmon 11 produces a rainbow-like jet in the collected images for the resonance conditions of FIG. 1B (see FIGS. 9A, 9B, 10A and 10B). These illustrate broad band excitation wherein the color spread reflects the surface plasmon dispersion and the energy dependant velocities (d ω/dk). FIGS. 10A-10D illustrates surface plasmon decay lengths. FIG. 10A shows the appearance of the surface plasmon 11 spread as a function of wavelength from a detected region of a specimen. FIG. 10B illustrates the intensity variation as a function of wavelength for a series of cross sectional lines shown in FIG. 10A. FIG. 10C shows the exponential decay behavior for a variety of wavelengths of emitted leakage radiation. FIG. 10D shows decay length as a function of wavelength of the leakage radiation.

The leakage radiation 22 (See FIG. 1A) emitted in the glass substrate 16 by the surface plasmons 11 traveling at the air 12/metal 14/interface 18 are characterized by a well-defined emission angle $\theta_{sp}$ for every wavelength. The value $\theta_{sp}$ is greater than the critical angle in the glass. Therefore, elements in optical contact with the substrate (the silver 14) are necessary to avoid total internal reflection of the leakage radiation 22 ("LR") within the substrate structure. This is achieved by an index-matched immersion objective 20 in contact with the substrate (the silver 14). The objective is part of a conventional inverted optical microscope (not shown) focused on the metal 14/glass 16/interface 18. The leakage radiation 22 is focused by objective lens 20 and then recorded by a radiation sensor capable of detecting and analyzing visible and IR light, such as, CCD camera 24 placed in the image plane. We used the same objective 20 as part of the system 10 to excite the surface plasmons 11 in a variant of the Kretschmann configuration. There are several key advantages for using the objective 20 with the immersion oil 26 to excite the surface plasmons 11 over the standard prism. First, in order to visualize the leakage radiation 22 (LR), the surface plasmons excitation area must be smaller than the SP propagation length, which is achieved by focusing the illumination beam 13. As a result of the focusing, a broad distribution of rays or wavevectors are impinging on the glass 16/silver 14/interface 18. For a given wavelength, an associated wavevector will be responsible for surface plasmon excitation, while the others will be reflected or transmitted through the silver 14. But, if the illumination light beam 13 is composed of a white-light continuum, virtually all wavelengths will be able to couple into the surface plasmons 11.

The oil immersion objective 20 we used has a most preferred numerical aperture (N.A.) of 1.4, meaning that the angular spread ranges between 0° to 68°. The SP excitation angles for wavelengths throughout the visible are confined within a few degrees around 45°. Therefore, if the full N. A. of the objective 20 is used, only a small fraction of the light 13 will be converted into the surface plasmons 11; and the overwhelming remaining part will be reflected or transmitted through the silver film 14. Instead of completely filling the back-aperture of the objective 20, a small beam of the collimated white-light beam 13 was adjusted within the back-aperture of the objective 20 as depicted in FIG. 1A. The angle of the reflected light beam 30 emerging from the objective 20, and the angular spread of the light beam 30 was controlled by adjusting the incident beam 13 with respect to optical axis 32.

The incident white-light beam 13 continuum was produced by the output of a Coherent MIRA regeneratively amplified Ti:Sapphire laser system (not shown). The beam 13 is created through well-known methods, in particular by focusing the 800 nm pulses into a small piece of sapphire (50 fs/pulse at 250 kHz). The white light beam 13 produced in this manner is generally easier to manipulate, collimate, and focus than other typical white light sources. The polarization of the beam 13 was controlled by a conventional multi-wavelength waveplate (not shown). The asymmetric plasmonic films were produced by thermally evaporating about 45±5 nm thick silver films on cleaned ones of the glass cover slips 16.

Figure 2A:
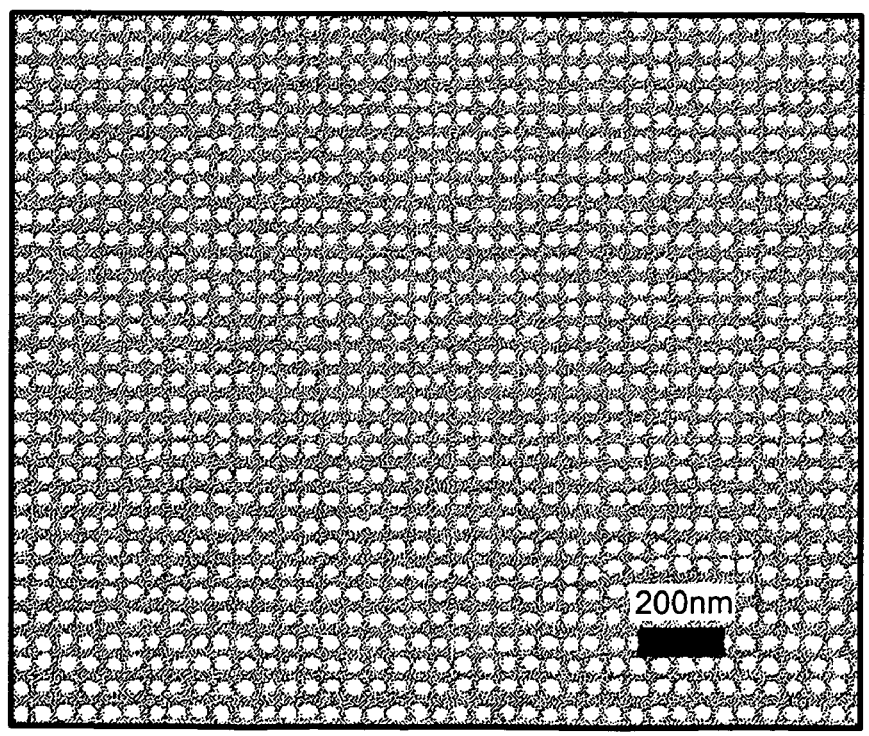
FIG. 2A illustrates sensing of particles in a two-dimensional array.
Figure 2B:
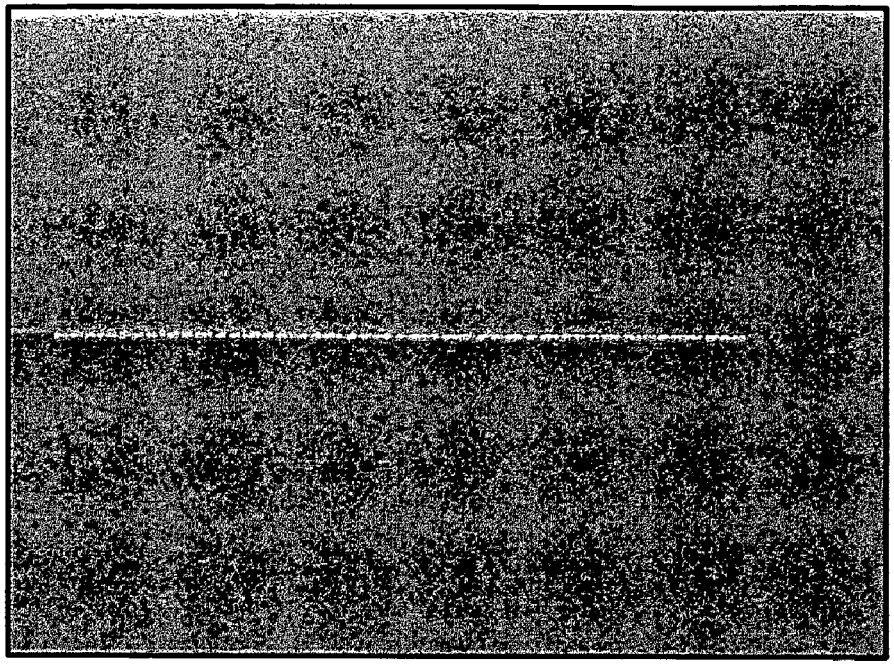
FIG. 2B illustrates sensing a line of particles and FIG. 2C illustrates sensing larger particles along a line.
Figure 2C:
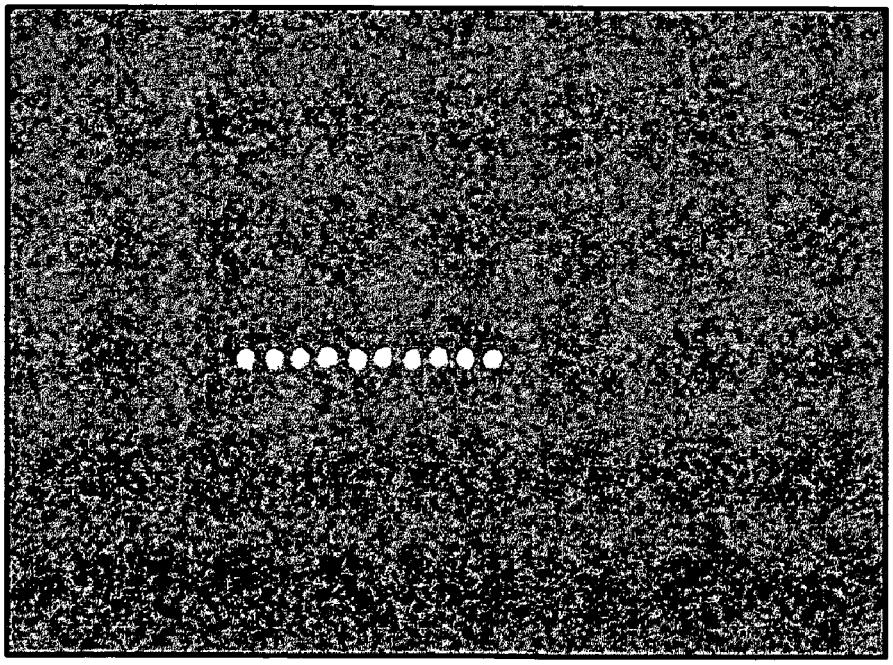
Figure 3:
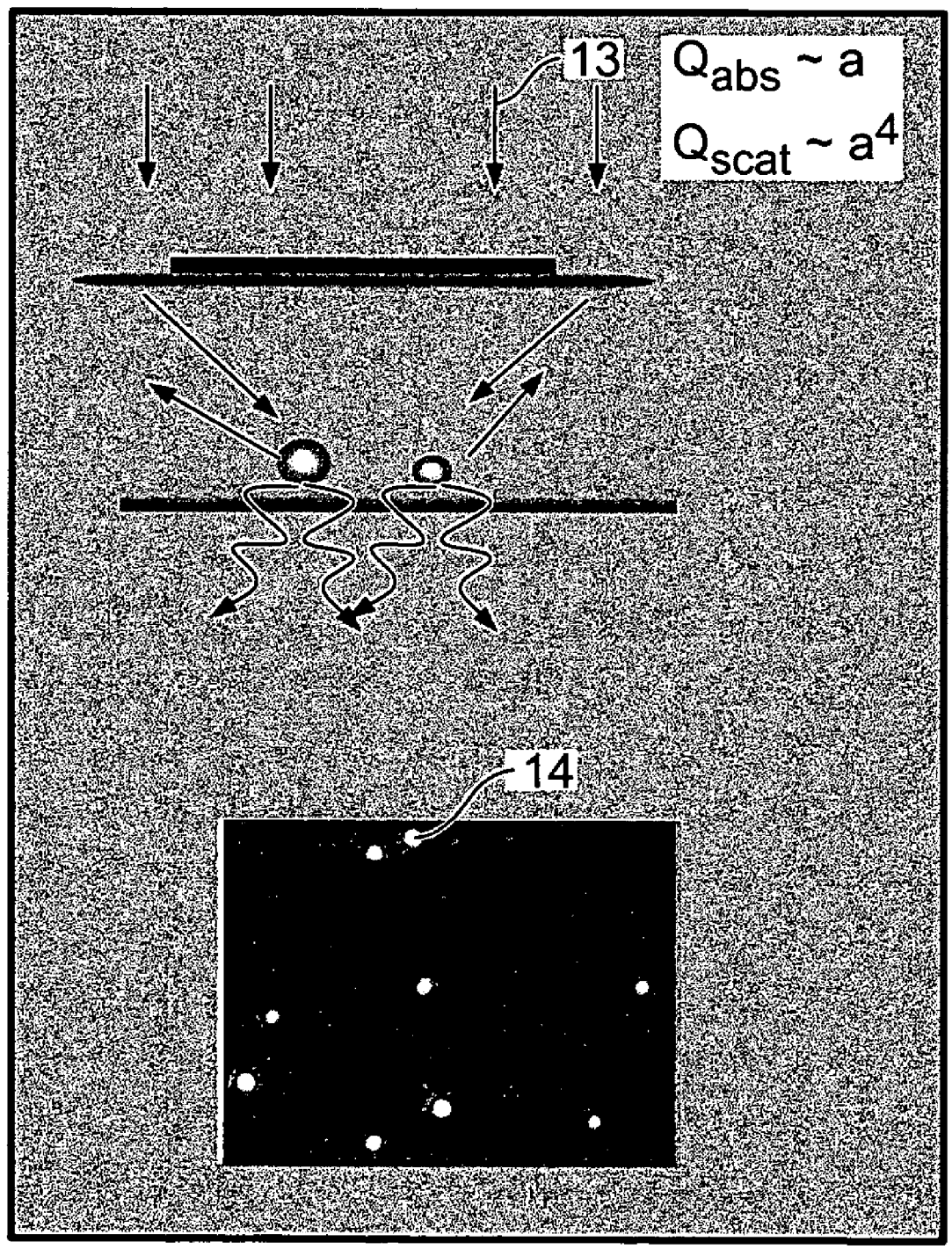
FIG. 3 illustrates dark field spectroscopy using surface plasmons to sense isolated nanoparticles.

The resulting plasmon sensor system 10 is a highly sensitive device which can analyze and detect extremely small quantities of adsorbates on a metallic conducting material. Various features of surface plasmon sensors can be exploited to determine the presence and amount of adsorbates and even near surface constituents which are different than the matrix of the material being studied. An example of plasmonics is shown in FIGS. 2A-2C which demonstrates spatial sensitivity to particle size and interparticle spacing. In FIG. 3 is a "dark-field spectroscopy" image where the light 13 imparts a beam mask 15; and then the nanoparticles shown are detected by the surface plasmon 11 scattering from the nanoparticles 17 in layer 19 with no forward illumination light transmitted.

Figure 4:
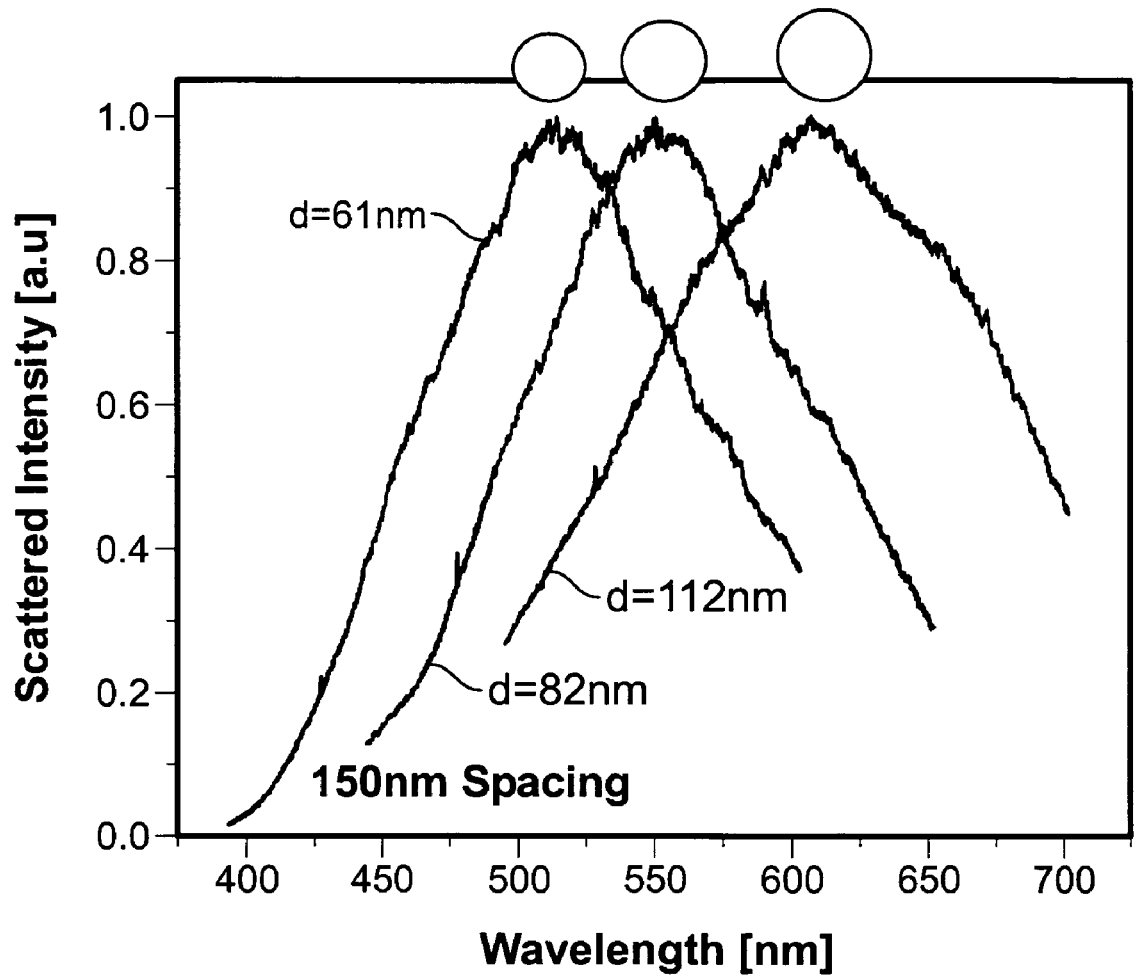
FIG. 4 illustrates blue-shift of surface plasmon resonance as a function of particle size.
Figure 5A:
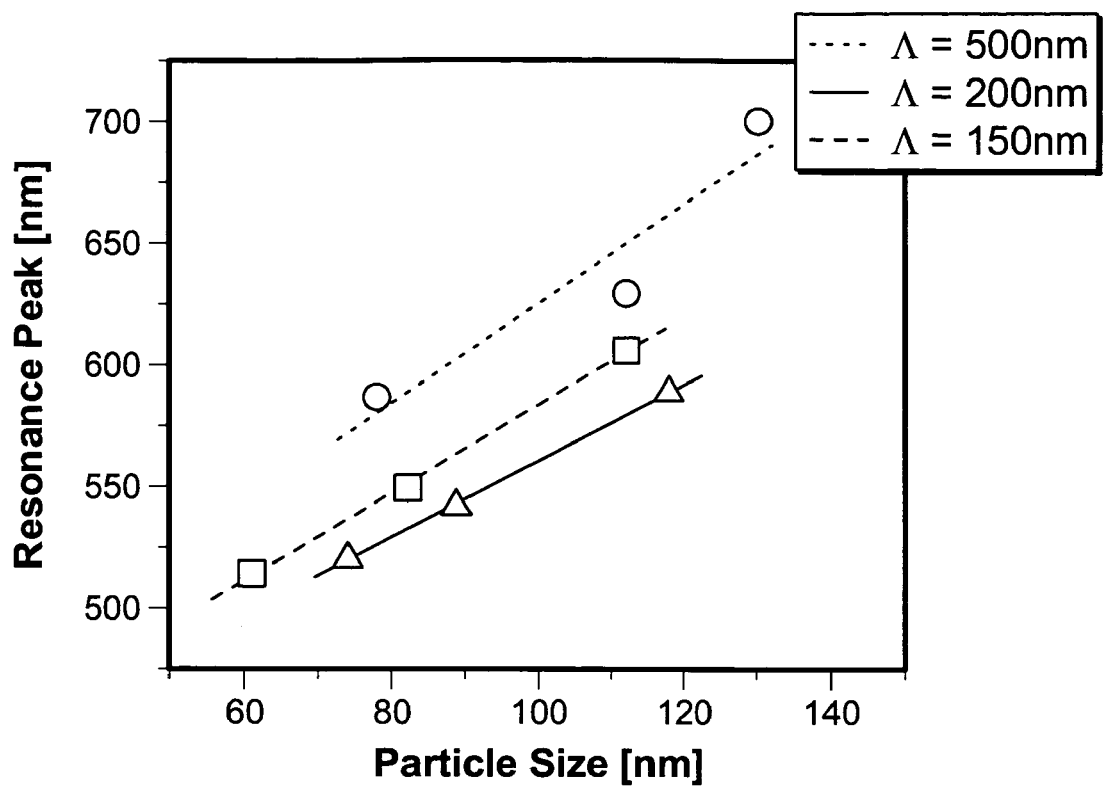
FIG. 5A illustrates the effect of increased damping of surface plasmons on resonance peak position as a function of particle spacing.
Figure 5B:
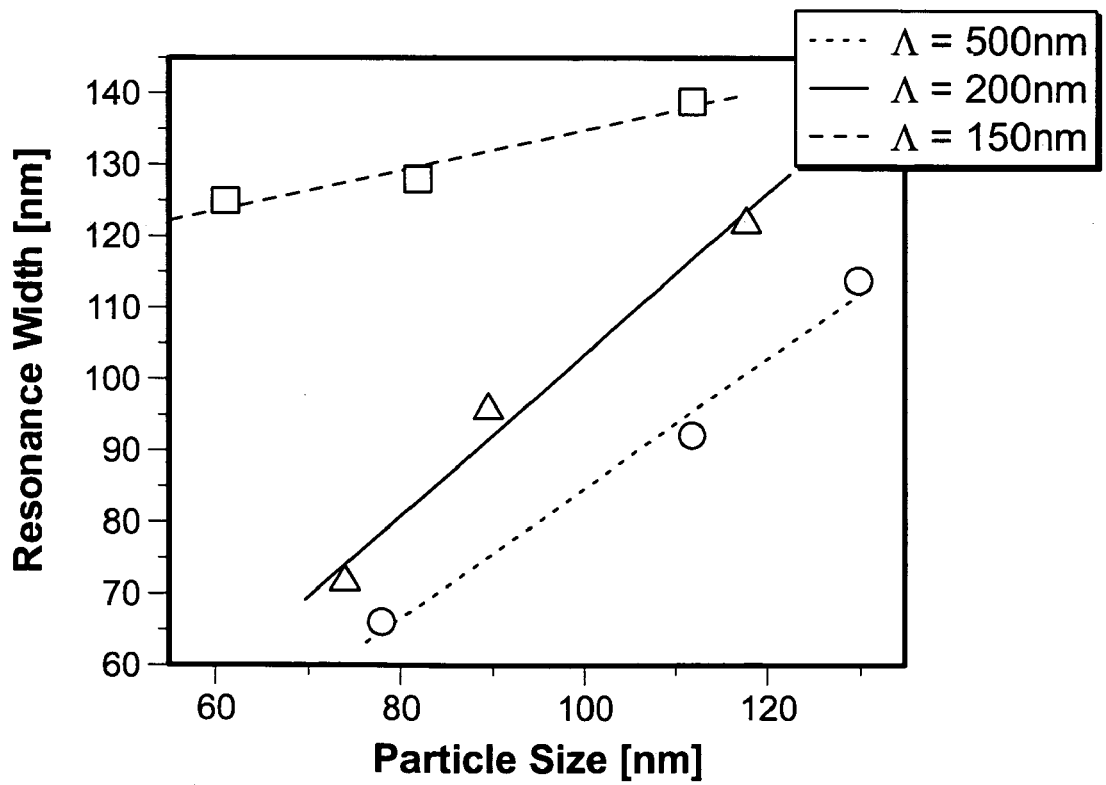
FIG. 5B the effect on resonance peak width.
Figure 6A:
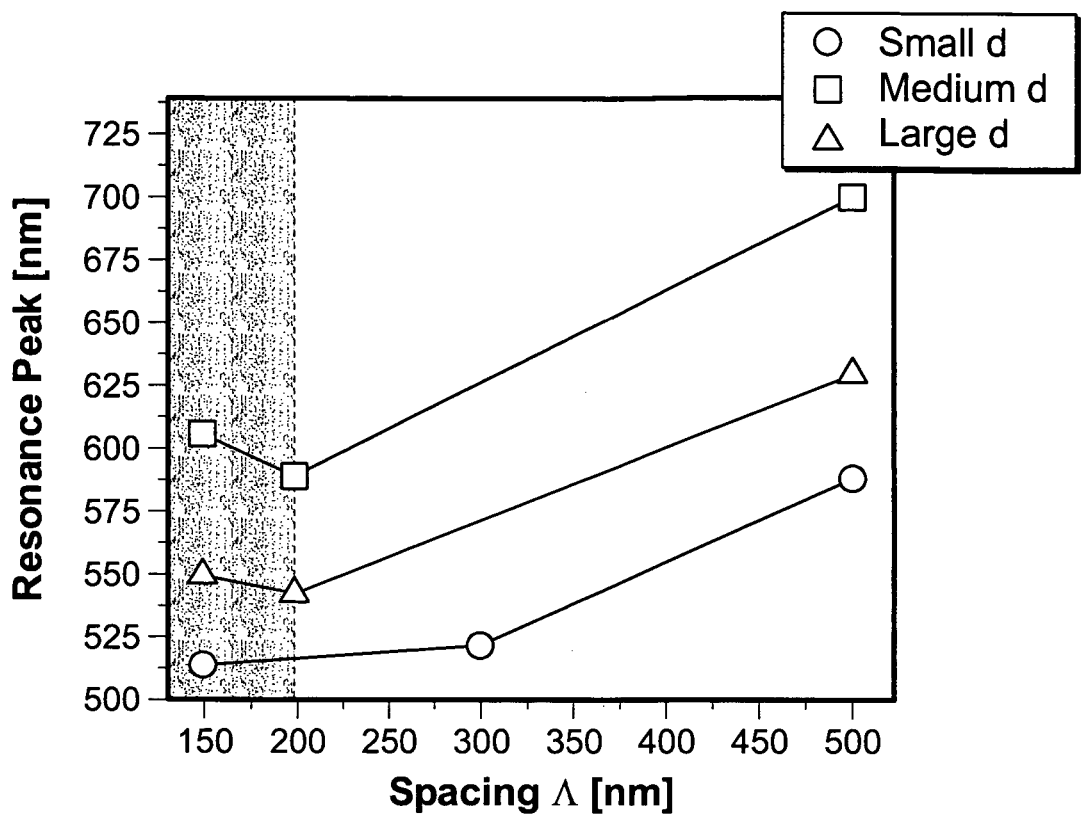
FIG. 6A illustrates the effect of blue-shift of surface plasmon leakage radiation on resonance peak position for different particle sizes and FIG. 6B the effect on resonance width.
Figure 6B:
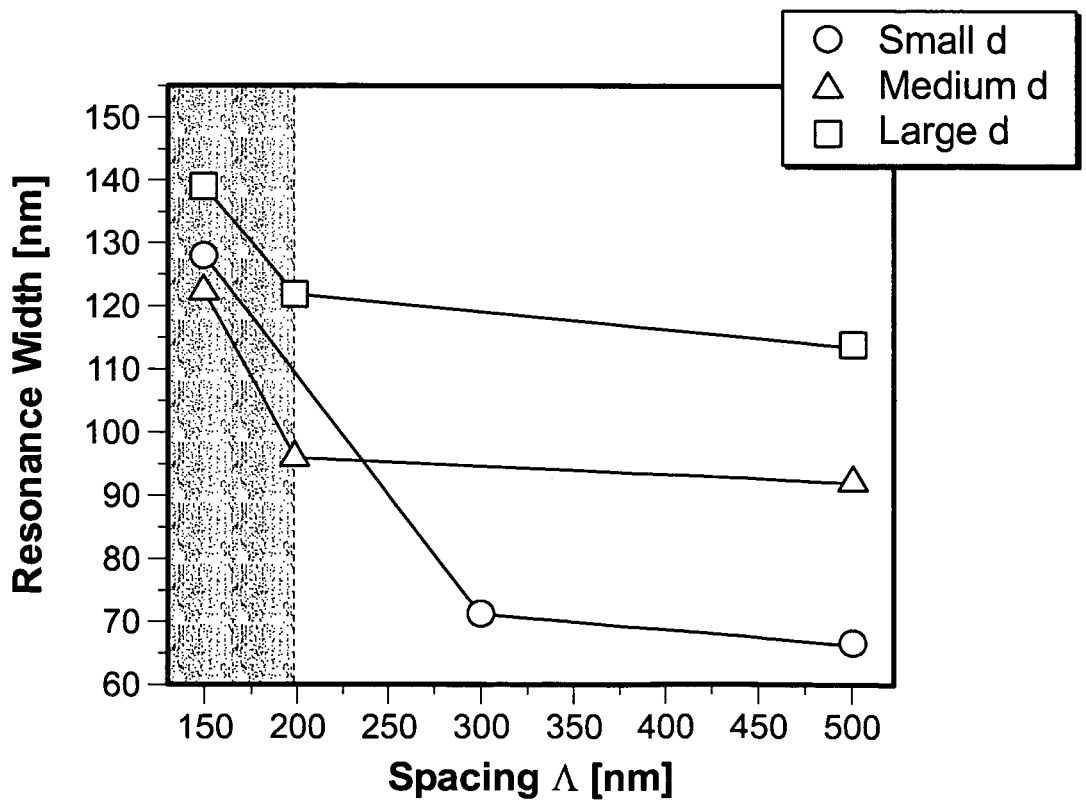

Further work is illustrated in FIG. 4, which shows a blue-shift in the plasmon resonance value for decreasing particle size and also the narrowing of the resonance for decreasing particle size (reduced plasmon damping). In FIGS. 5A and 5B is shown the characteristic increased damping for small spacing in terms of resonance peak location and resonance peak width. In FIGS. 6A and 6B is shown the influence of interparticle spacing for a two-dimensional array. A far field effect is shown in the form of a grating effect and blue shift for spacings greater than 200 nm. A near field coupling is shown for a red shift of the plasmon for spacings less than 200 nm. An increased plasmon damping occurs in the near field. In FIGS. 7A and 7B is shown the influence of interparticle spacing for a one-dimensional array.

Figure 8A:
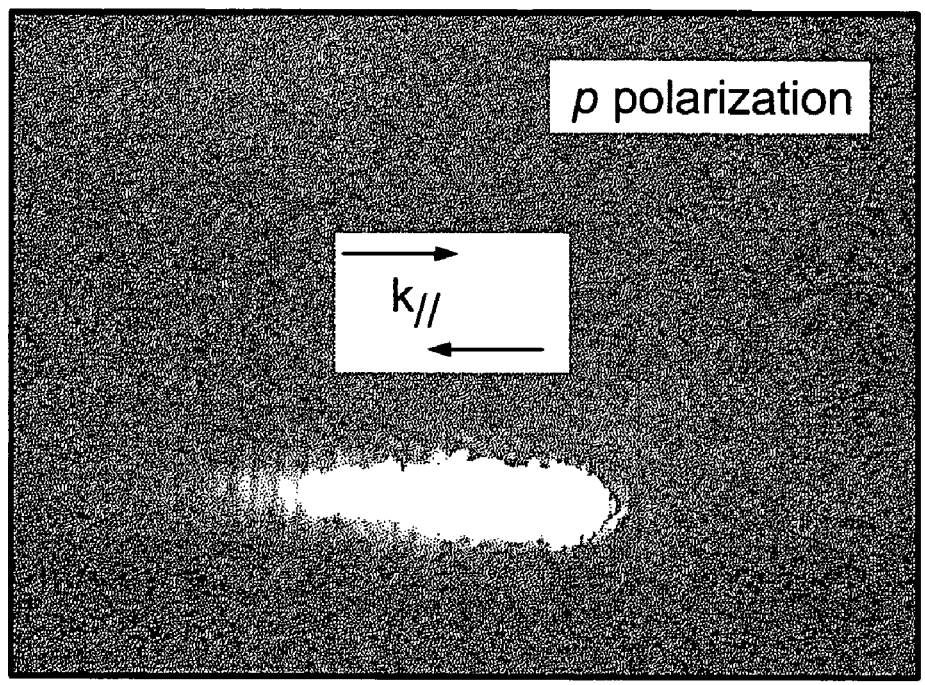
FIG. 8A shows p-type light polarization effect on leakage radiation and FIG. 8B shows the effect for s-type polarization.
Figure 8B:
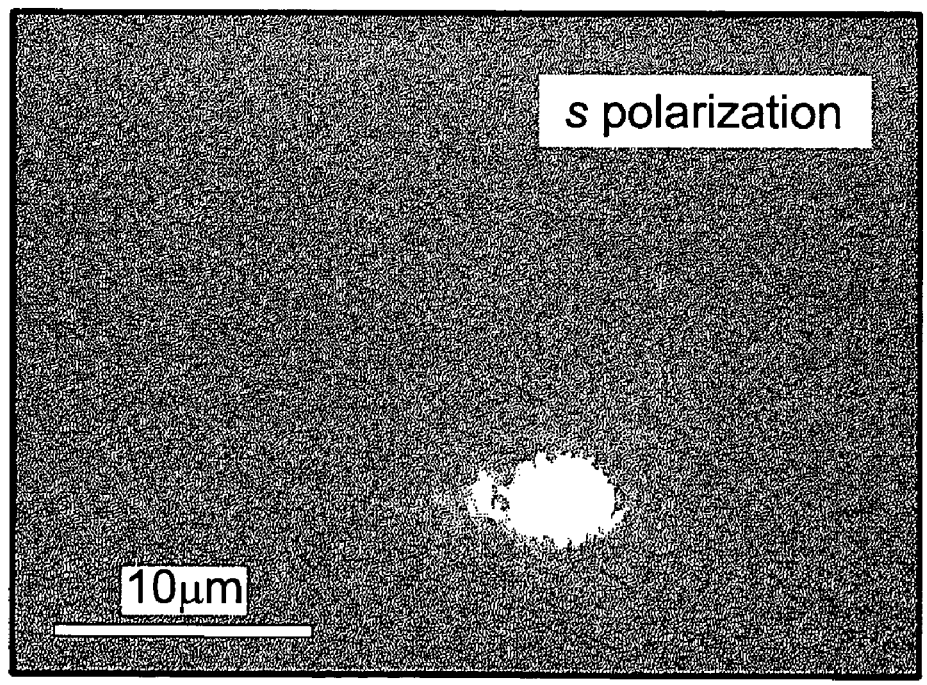
Figure 9A:
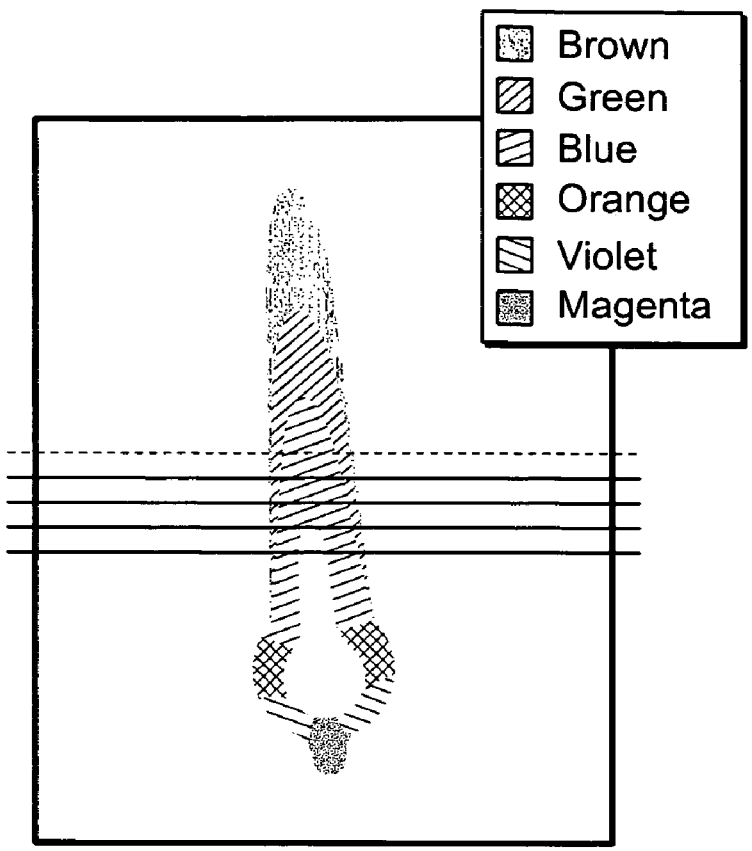
FIG. 9A illustrates broad band excitation producing a plasmon rainbow leakage radiation spectrum with changing colors of light and FIG. 9B shows for use of only s-type polarized light.
Figure 9B:
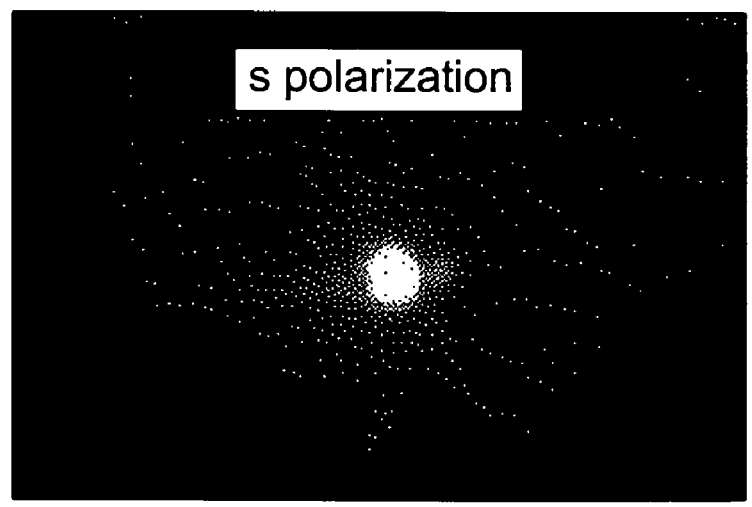

One embodiment of the invention of FIGS. 1A-1C is shown in FIGS. 8A and 8B, where polarization sensitivity can be used to advantage with "p" type polarization for the light 13 which results in the illuminated signature for plasmon excitation while FIG. 8B shows the signature for "s" type polarized light 13. The spectra shown are for the silver 14 layer of 50 nm thickness, the light 13 is 532 nm; and the NA of the objective 20 is 1.4 for a magnification of 60X.

Figure 11:
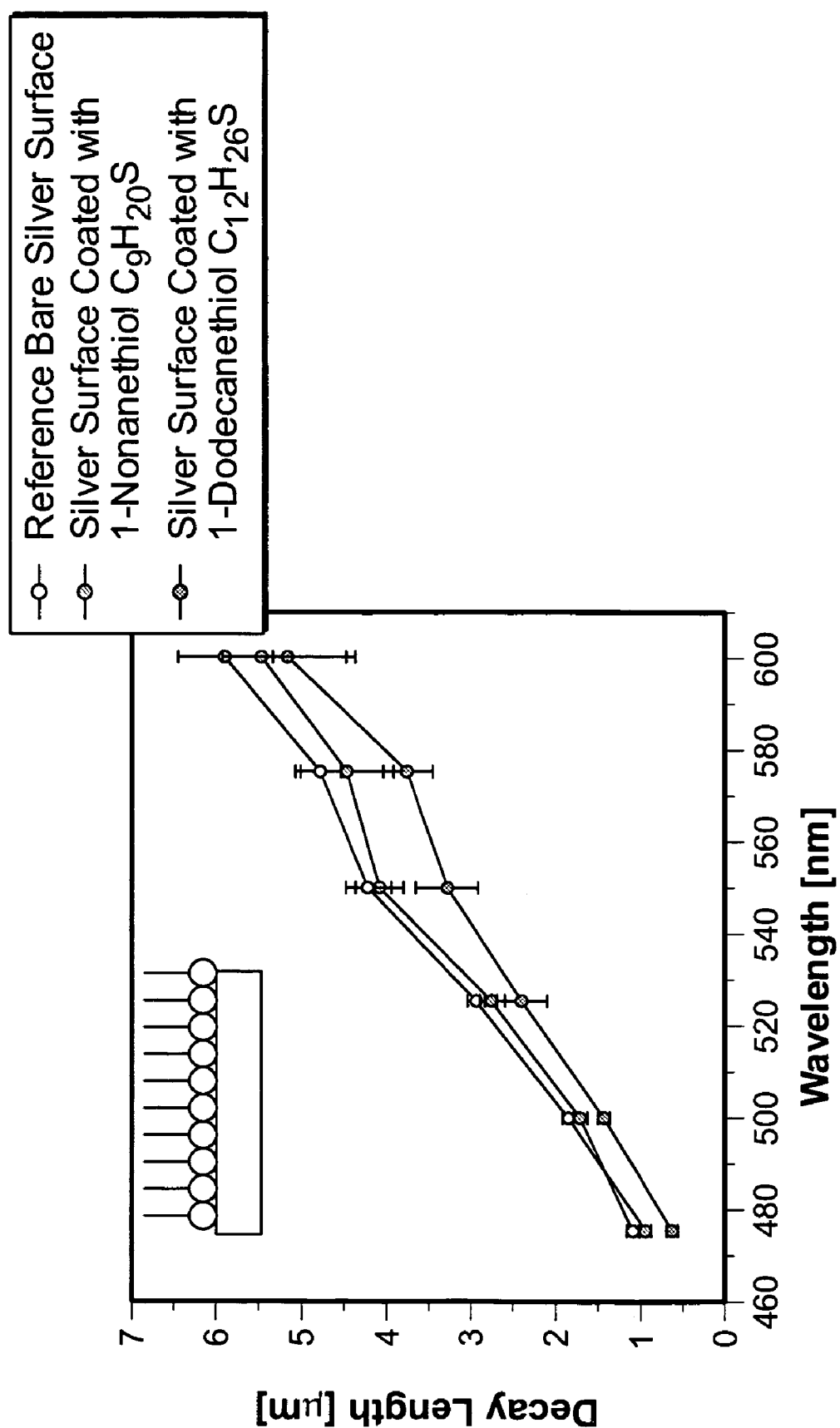
FIG. 11 shows an example sensor with data for various surface coatings.

FIG. 11 illustrates the surface plasmon decay length for several example substrates and coated layers. Note the systematic decline in decay length as the reference silver 14 is coated with 1-Nonanethiol and 1-Dodecanethiol.

Figure 12A:
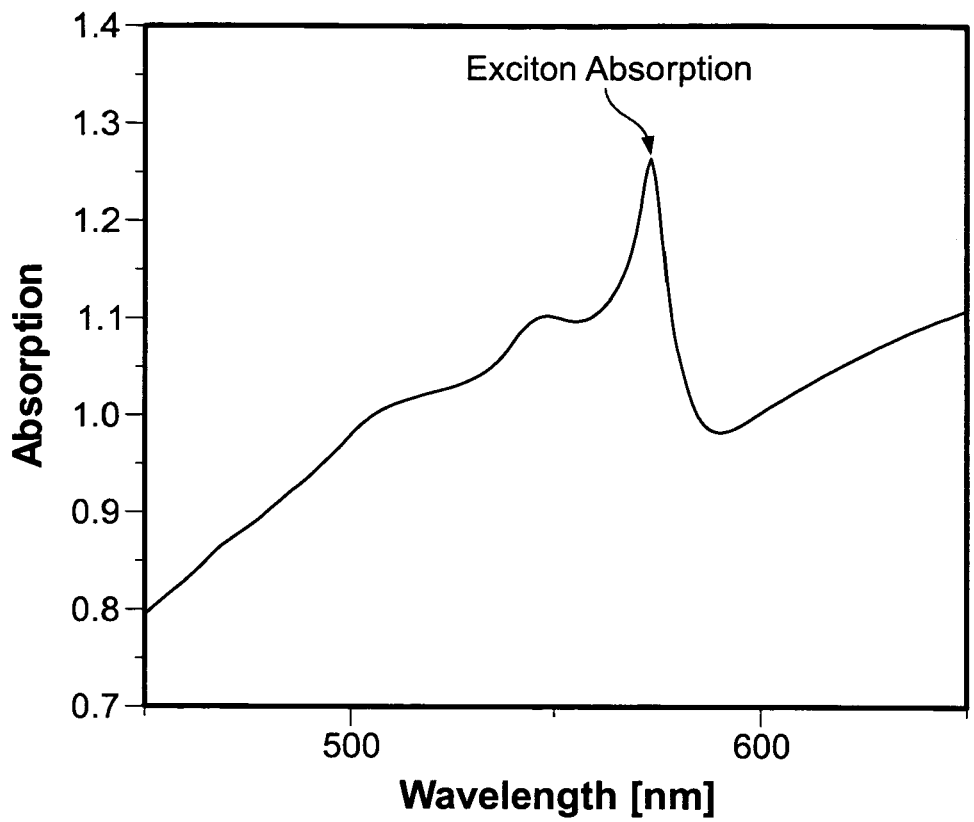
FIG. 12A illustrates absorption versus wavelength for radiation leakage.
Figure 12B:
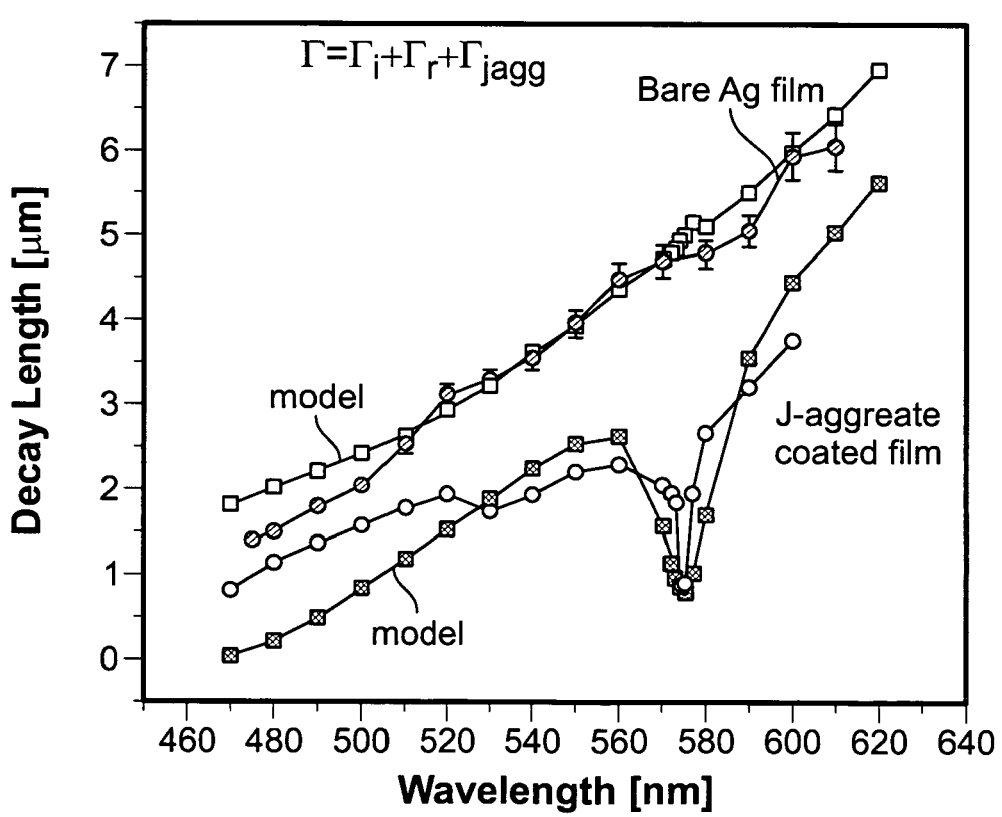
FIG. 12B illustrates decay length of the plasmon versus leakage radiation for a reference Ag film and a J-aggregate coated film.

FIGS. 12A and 12B illustrate another example of absorption spectroscopy for the system 10 wherein conventional J-aggregates are present on the silver 14.

Figure 13A:
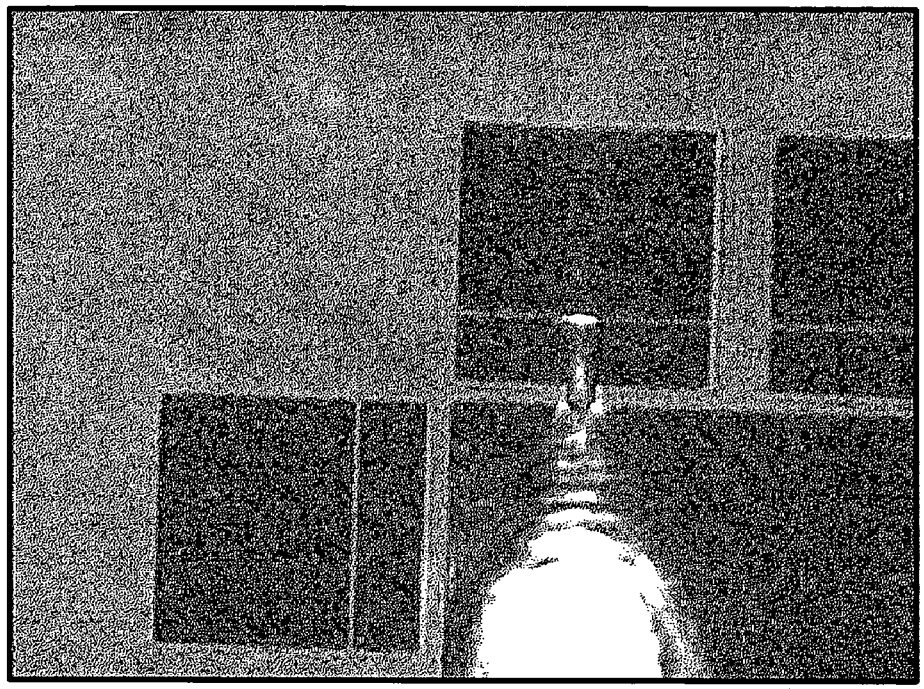
FIG. 13A illustrates a plasmon rainbow jet for a device microstructure.
Figure 13B:
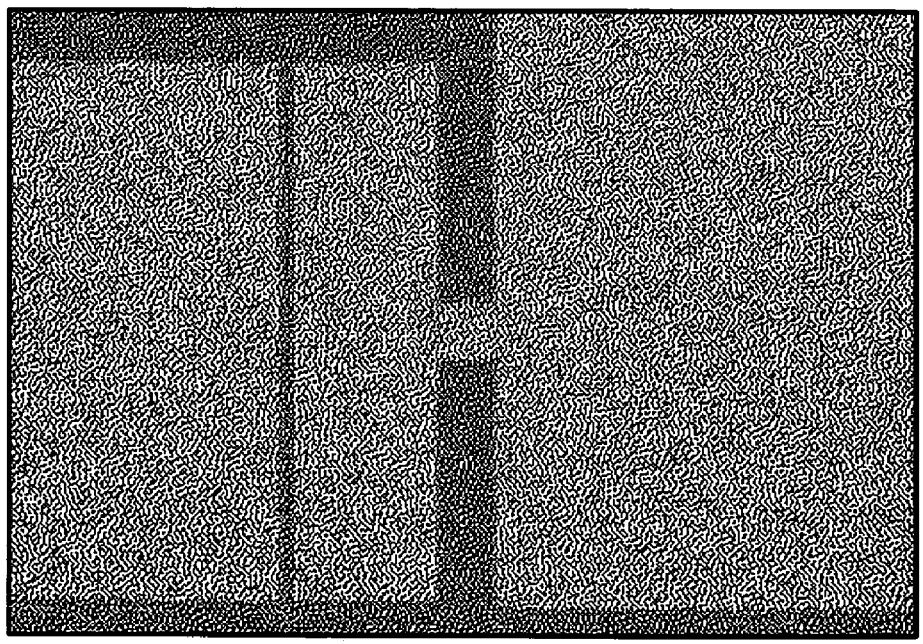
FIG. 13B shows a bridge section for the device of FIG. 13A.
Figure 13C:
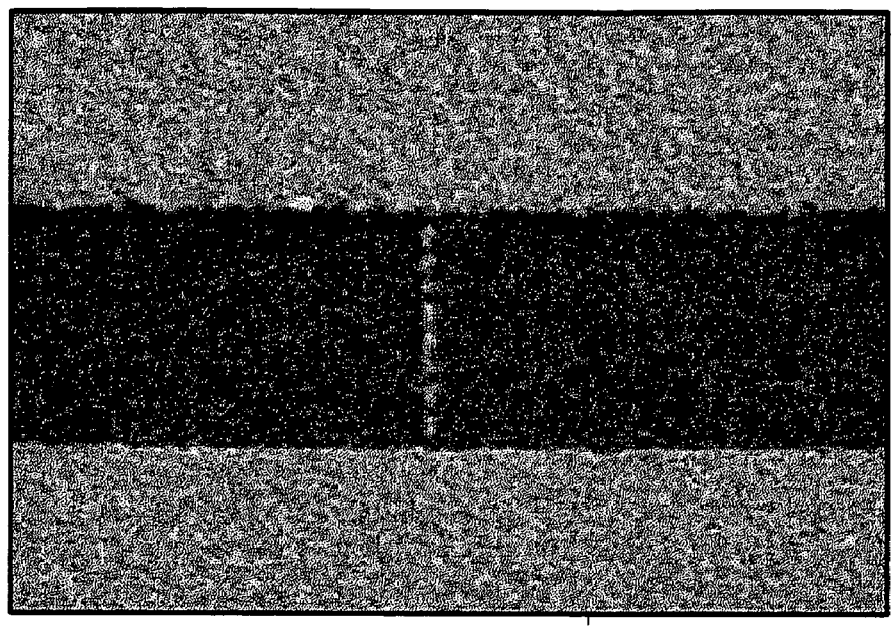
FIG. 13C shows another bridge structure detail for the device of FIG. 13A.
Figure 13D:
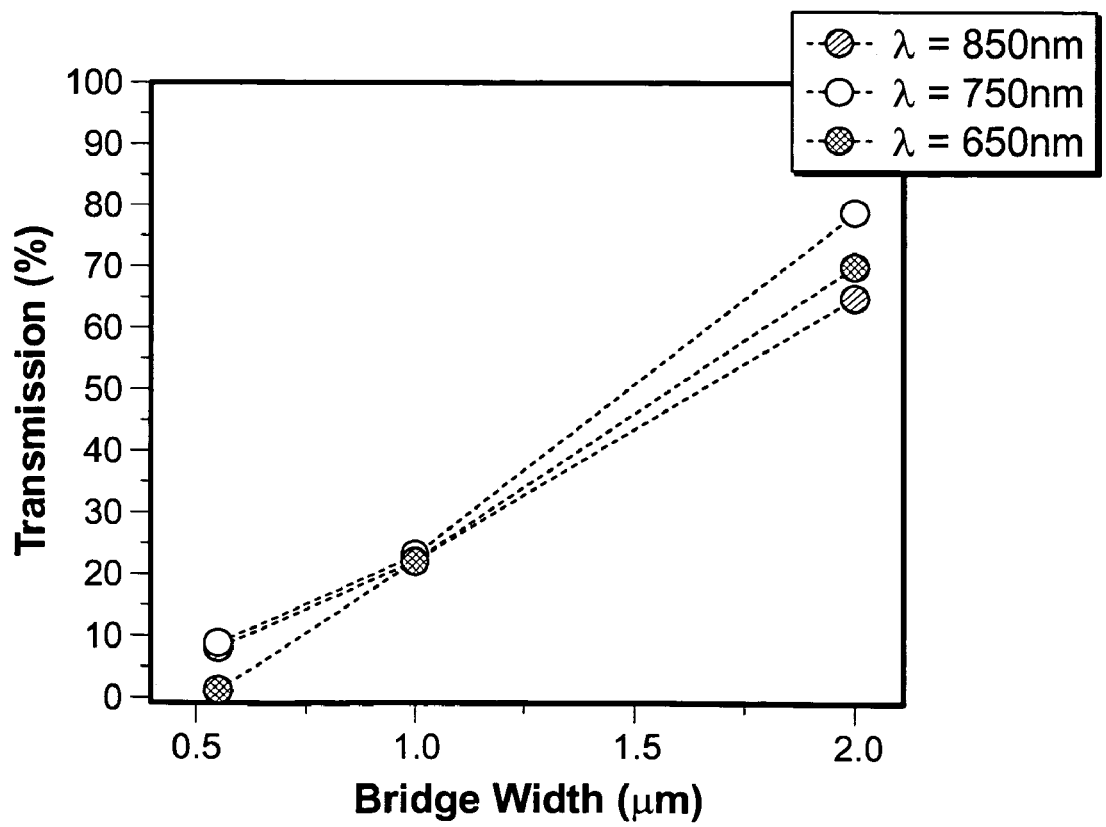
FIG. 13D shows transmission percent versus bridge width for different leakage radiation wavelengths.

FIGS. 13A-13D illustrate surface plasmon transmission characteristics for various submicron structures, such as are typically present in electronics arts and the like. FIG. 13A shows the overall leakage radiation as a "rainbow-jet" dispersion. FIG. 13B shows a bridge structure in the electronic device, FIG. 13C shows another bridge structure and FIG. 13D shows percent transmission as a function of bridge width for leakage radiation wavelengths of 650 nm, 750 nm and 850 nm.

It should be understood that various changes and modifications referred to in the embodiment described herein would be apparent to those skilled in the art. Such changes and modifications can be made without departing from the spirit and scope of the present invention. For instances, the femtosecond laser system used to produce the white-light continuum can be replaced by a simple gas bulb (halogen, etc.), or light emitting diode (LED), or emissive element (tungsten or carbon for example), etc. Similarly, the broad spectrum of wave vectors produced by the objective lens can also be produced by a defect on the film (engineered or natural) that is sub-wavelength in dimensions, or by the proximity of a near-field probe (with or without aperture). Similarly, a solid immersion lens or other high numerical aperture optic can readily replace the oil immersion objective used here. Similarly, the research grade CCD can be replaced by simpler devices, such as a digital camera, diode, or integrated hand-held or on-chip spectrograph. The inverted microsocope is used only for versatility and exploring a range of initial optical configurations during research. Now optimized, it can be eliminated in a commercial system. Changes to the detection of the broadband leakage radiation can also be readily envisioned by those skilled in the art, e.g. by avoiding leakage radiation collection by the objective lens.

What is claimed is:

1. A plasmon excitation and sensor system for detecting surface material on a substrate, comprising:
   a source of light for exciting asymmetrical surface plasmons in the surface material;
   an optical coupling element receiving the light from said source and then further receiving and outputting leakage radiation emitted by the surface plasmons interacting with the surface material; and
   a radiation sensor for receiving and analyzing the leakage radiation to determine characteristics of the surface material.

2. The plasmon excitation and sensor system as defined in claim 1 wherein the source of light comprises at least one of a white-light continuum and a discrete set of wavelengths.

3. The plasmon excitation and sensor system as defined in claim 1 wherein a metal film rests on the substrate which is transparent to light energies from the source and to the leakage radiation.

4. The plasmon excitation and sensor system as defined in claim 1 wherein the leakage radiation are collected by an appropriate optical element, including at least one of an immersion objective lens and a hemispheric lens.

5. The plasmon excitation and sensor system as defined in claim 1 wherein the leakage radiation ranges from the visible to infrared region.

6. The plasmon excitation and sensor system as defined in claim 1 wherein spread of surface plasmon wavevectors matches selected correct energies of the source of light as defined by a plasmon dispersion relation.

7. The plasmon excitation and sensor system as defined in claim 1 wherein the radiation sensor comprises at least one of a CCD camera and another light sensitive detector.

8. The plasma excitation and sensor system as defined in claim 1 wherein polarization of the source of light matches surface plasmon excitation conditions.

9. The plasma excitation and sensor system as defined in claim 1, wherein a asymmetrical broadband plasmon can be excited, enabling high bandwidth photonic applications.

10. The plasmon excitation and sensor system as defined in claim 1 wherein the leakage radiation is characterized in terms of surface plasmon losses.

11. The plasmon excitation and sensor system as defined in claim 1 wherein the leakage radiation can be categorized in accordance with surface plasmon wavelength and lateral surface plasmon propagation distances.

12. The plasmon excitation and sensor system as defined in claim 1 wherein properties of the leakage radiation are characteristic of a chemical signature of the surface material.

13. A method of sensing characteristics of an analyte on or near an asymmetrical plasmonic surface, comprising the steps of:
    applying light selected from the group of a white-light continuum and a set of discrete wavelengths to a substrate with analyte disposed at least one of adsorbed on a metal surface and near a metal surface;
    forming asymmetrical surface plasmons in the substrate;
    sensing leakage radiation emitted by decaying of the surface plasmons; and
    analyzing the leakage radiation to characterize the analyte.

14. The method as defined in claim 13 wherein the substrate comprises at least one of a metal and another material supporting the asymmetrical surface plasmon.

15. The method as defined in claim 13 wherein an excitation area on the substrate is at least one of smaller and comparable to a surface plasmon propagation distance.

16. The method as defined in claim 15 wherein a small excitation area is achieved through a focusing element.

17. The method as defined in claim 13 wherein the white-light continuum and the discrete set of wavelengths comprises polarized light for most efficient excitation of the surface plasmon.

18. A plasmon excitation and sensor system for detecting surface features disposed on a substrate, comprising:
    a source of focused and polarized light;
    at least one of an immersion objective lens and another focusing element in optical contact with the surface feature and for receiving at least one of a white-light continuum and a discrete set of wavelength and coupling the white-light continuum and the discrete set of wavelengths to an asymmetrical surface plasmon in the substrate and the surface features;
    the at least one of immersion objective lens and another focusing element further operating to receive leakage radiation emitted by surface plasmons created in the substrate by the light and outputting the leakage radiation; and
    at least one of a CCD camera system and another optical detector for receiving and analyzing the leakage radiation to characterize the surface features.

* * * * *